(12) United States Patent
Wang et al.

(10) Patent No.: US 10,568,991 B2
(45) Date of Patent: Feb. 25, 2020

(54) CATHETER INCLUDING LEAK RESISTANT PROXIMAL SHAFT

(71) Applicant: Covidien LP, Mansfield, MA (US)

(72) Inventors: Edwin Wang, Tustin, CA (US); Komonn Lim, Lake Forest, CA (US)

(73) Assignee: Covidien LP, Mansfield, MA (US)

( * ) Notice: Subject to any disclaimer, the term of this patent is extended or adjusted under 35 U.S.C. 154(b) by 133 days.

(21) Appl. No.: 14/824,323

(22) Filed: Aug. 12, 2015

(65) Prior Publication Data

US 2017/0043060 A1 Feb. 16, 2017

(51) Int. Cl.
*A61L 29/08* (2006.01)
*A61M 25/00* (2006.01)
*A61L 29/02* (2006.01)

(52) U.S. Cl.
CPC .............. *A61L 29/085* (2013.01); *A61L 29/02* (2013.01); *A61M 25/0014* (2013.01); *A61M 25/0045* (2013.01); *A61M 25/0097* (2013.01); *A61L 2420/00* (2013.01)

(58) Field of Classification Search
CPC .. A61M 2025/0046; A61M 2025/0047; A61M 2025/0098; A61M 25/0045; A61M 25/0014; A61M 39/10; A61M 25/0097; A61M 25/005; A61M 25/0051; A61M 25/0052; A61M 25/0053; A61M 39/08; A61M 39/12; A61M 25/0625; A61M 2025/0048; B32B 1/08; B32B 3/00; B32B 7/12
See application file for complete search history.

(56) References Cited

U.S. PATENT DOCUMENTS

| | | | | |
|---|---|---|---|---|
| 4,636,346 A | * | 1/1987 | Gold | ............... A61M 25/001 138/109 |
| 4,806,182 A | * | 2/1989 | Rydell | ............. A61M 25/0014 138/109 |
| 5,167,647 A | | 12/1992 | Wijkamp et al. | |

(Continued)

FOREIGN PATENT DOCUMENTS

| | | |
|---|---|---|
| FR | 2092970 | 1/1972 |
| WO | 2014210427 A1 | 12/2014 |

OTHER PUBLICATIONS

Extended European Search Report from counterpart European Application No. 16181962.8, dated Jan. 19, 2017, 9 pp.

(Continued)

*Primary Examiner* — Kami A Bosworth
*Assistant Examiner* — Alexandra Lalonde
(74) *Attorney, Agent, or Firm* — Shumaker & Sieffert, P.A.

(57) ABSTRACT

A catheter may include a hypotube defining an inner circumferential surface, an outer circumferential surface, and an end. The hypotube may include a metal or alloy. The catheter also may include an inner liner attached to the inner circumferential surface of the hypotube and extending beyond the end of the hypotube, and the inner liner may include a fluoropolymer. The catheter further may include a hub and a single bonding layer attached to the outer circumferential surface of the hypotube and bonded to the hub. The single bonding layer may include a polyamide, a polyether-co-polyamide, or polyurethane and is the only layer between the outer circumferential surface of the hypotube and the hub.

17 Claims, 3 Drawing Sheets

(56) References Cited

U.S. PATENT DOCUMENTS

| | | | |
|---|---|---|---|
| 5,358,493 A * | 10/1994 | Schweich, Jr. | ... A61M 25/0013 604/264 |
| 5,569,200 A * | 10/1996 | Umeno | A61M 25/0045 604/102.02 |
| 5,766,151 A * | 6/1998 | Valley | A61B 17/00234 604/103.07 |
| 5,860,963 A | 1/1999 | Azam et al. | |
| 7,662,144 B2 * | 2/2010 | Chan | A61M 25/0009 604/264 |
| 7,704,245 B2 | 4/2010 | Dittman et al. | |
| 8,348,925 B2 | 1/2013 | Fischell et al. | |
| 8,403,896 B2 | 1/2013 | Leeflang et al. | |
| 2002/0128631 A1 | 9/2002 | Hayman | |
| 2003/0220628 A1 | 11/2003 | Klisch et al. | |
| 2005/0283134 A1 | 12/2005 | Chan et al. | |
| 2006/0030835 A1 * | 2/2006 | Sherman | A61F 2/958 604/526 |
| 2006/0224113 A1 * | 10/2006 | van Sloten | A61M 25/0009 604/103.1 |
| 2006/0264904 A1 | 11/2006 | Kerby et al. | |
| 2007/0250150 A1 * | 10/2007 | Pal | A61F 2/95 604/538 |
| 2011/0238041 A1 | 9/2011 | Lim et al. | |
| 2014/0358123 A1 * | 12/2014 | Ueda | A61M 25/0097 604/510 |
| 2015/0265806 A1 * | 9/2015 | Kawaguchi | A61M 25/0097 604/539 |

OTHER PUBLICATIONS

First Office Action and Search Report, and translation thereof, from counterpart Chinese Application No. 201610656471.7, dated Dec. 24, 2018, 19 pp.

Examination Report from counterpart European Application No. 16181962.8, dated Dec. 11, 2018, 5 pp.

Response to Examination Report dated Dec. 11, 2018, from counterpart European Application No. 16181962.8, filed Apr. 12, 2019, 15 pp.

Second Office Action, and English translation thereof, from counterpart Chinese Application No. 201610656471.7, dated May 17, 2019, 21 pp.

* cited by examiner

CATHETER INCLUDING LEAK RESISTANT PROXIMAL SHAFT

TECHNICAL FIELD

The disclosure relates to medical catheters.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters that include a hypotube and an inner liner attached to an inner circumferential surface of the hypotube and extending beyond the end of the hypotube. The inner liner may include a fluoropolymer. The catheter also may include a single bonding layer attached to an outer circumferential surface of the hypotube. The bonding layer may bond a hub to the hypotube. In some examples, the bonding layer and the inner liner may each extend beyond an end of the hypotube, and the bonding layer may attach to the inner liner. This disclosure also describes example methods of forming catheters and methods of using catheters.

Clause 1: In some examples, a catheter includes a hypotube defining an inner circumferential surface, an outer circumferential surface, and an end. The hypotube may include a metal or alloy. The catheter also may include an inner liner attached to the inner circumferential surface of the hypotube and extending beyond the end of the hypotube, and the inner liner may include a fluoropolymer. The catheter further may include a hub and a single bonding layer attached to the outer circumferential surface of the hypotube and bonded to the hub. The single bonding layer may include a polyamide or a polyether-co-polyamide, and is the only layer between the outer circumferential surface of the hypotube and the hub.

Clause 2: In some examples of the catheter of clause 1, the single bonding layer consists essentially of the polyamide or the polyether-co-polyamide.

Clause 3: In some examples of the catheter of clause 1, the single bonding layer consists essentially of polyether-co-polyamide.

Clause 4: In some examples of the catheter of any one of clauses 1 to 3, the hub includes polypropylene.

Clause 5: In some examples of the catheter of any one of clauses 1 to 4, the hub is overmolded or adhesively bonded to the single bonding layer.

Clause 6: In some examples of the catheter of any one of clauses 1 to 5, the inner liner includes polytetrafluoroethylene (PTFE).

Clause 7: In some examples of the catheter of any one of clauses 1 to 6, the single bonding layer extends beyond the end of the hypotube and is bonded to the inner liner.

Clause 8: In some examples of the catheter of clause 7, wherein the single bonding layer extends beyond the end of the hypotube substantially the same distance as the inner liner extends beyond the end of the hypotube.

Clause 9: In some examples of the catheter of any one of clauses 1 to 8, the metal or alloy includes at least one of stainless steel or a nickel-titanium alloy.

Clause 10: In some examples of the catheter of any one of clauses 1 to 9, the hypotube includes a spiral-cut tube or slotted tube.

Clause 11: In some examples, a catheter includes a hypotube defining an inner circumferential surface, an outer circumferential surface, and an end. The hypotube may include a stainless steel or a nickel titanium alloy. The catheter also may include an inner liner attached to the inner circumferential surface of the hypotube and extending beyond the end of the hypotube. The inner liner may include a polytetrafluoroethylene. The catheter further may include a hub and a single bonding layer attached to the outer circumferential surface of the hypotube and bonded to the hub. The single bonding layer may consist essentially of a polyamide or a polyether-co-polyamide, the single bonding layer may extend beyond the end of the hypotube substantially the same distance as the inner liner extends beyond the end of the hypotube and be bonded to the inner liner, and the single bonding layer may be the only layer between the outer circumferential surface of the hypotube and the hub and the only layer between the inner liner and the hub.

Clause 12: In some examples of the catheter of clause 11, the hub may include polypropylene.

Clause 13: In some examples of the catheter of clause 11 or 12, the hypotube may include a spiral-cut tube or slotted tube.

Clause 14: In some examples, a method may include attaching an inner liner to an inner circumferential surface of a hypotube. The inner liner may extend beyond the end of the hypotube and may include a fluoropolymer. The inner liner also may define an outer circumferential surface and an end. The hypotube may include a metal or alloy. The method also may include attaching a single bonding layer to the outer circumferential surface of the hypotube. The single bonding layer may include a polyamide or a polyether-co-polyamide. The method further may include attaching a hub to an outer surface of the single bonding layer. The single bonding layer may be the only layer between the hypotube and the hub.

Clause 15: In some examples of the method of clause 14, the single bonding layer consists essentially of the polyamide or the polyether-co-polyamide.

Clause 16: In some examples of the method of clause 14, the single bonding layer consists essentially of polyether-co-polyamide.

Clause 17: In some examples of the method of any one of clauses 14 to 16, the hub includes polypropylene.

Clause 18: In some examples of the method of any one of clauses 14 to 17, attaching the hub to the outer surface of the single bonding layer includes overmolding or adhesively bonding the hub to the outer surface of the single bonding layer.

Clause 19: In some examples of the method of any one of clauses 14 to 18, the inner liner includes polytetrafluoroethylene (PTFE).

Clause 20: In some examples of the method of any one of clauses 14 to 19, the single bonding layer extends beyond the end of the hypotube and is bonded to the inner liner.

Clause 21: In some examples of the method of clause 20, the single bonding layer extends beyond the end of the hypotube substantially the same distance as the inner liner extends beyond the end of the hypotube.

Clause 22: In some examples of the method of any one of clauses 14 to 21, the metal or alloy includes at least one of stainless steel or a nickel-titanium alloy.

Clause 23: In some examples of the method of any one of clauses 14 to 22, attaching the single bonding layer to the outer circumferential surface of the hypotube includes laminating the single bonding layer to the outer circumferential surface of the hypotube.

Clause 24: In some examples, a method may include introducing a distal end of a catheter body into a patient. The catheter body may include a hypotube defining an inner circumferential surface, an outer circumferential surface, and a proximal end. The hypotube may include a metal or alloy. The catheter body also may include an inner liner attached to the inner circumferential surface of the hypotube and extending beyond the proximal end of the hypotube, wherein the inner liner comprises a fluoropolymer. The inner liner may define at least one inner lumen. The catheter body may further include a hub and a single bonding layer attached to the outer circumferential surface of the hypotube and bonded to the hub. The single bonding layer may include a polyamide or a polyether-co-polyamide, and the single bonding layer may be the only layer between the outer circumferential surface of the hypotube and the hub. The method also may include guiding the distal end of the catheter body to a target tissue site within the patient.

Clause 25: In some examples of the method of clause 24, the method may further include introducing a guidewire in the patient, and guiding the distal end of the catheter body to the target tissue site may include guiding the distal end of the catheter body to the target tissue site over the guidewire.

Clause 26: In some examples of the method of clause 24 or 25, the single bonding layer consists essentially of the polyamide or the polyether-co-polyamide.

Clause 27: In some examples of the method of clause 24 or 25, the single bonding layer consists essentially of polyether-co-polyamide.

Clause 28: In some examples of the method of any one of clauses 24 to 27, the hub includes polypropylene.

Clause 29: In some examples of the method of any one of clauses 24 to 28, the inner liner includes polytetrafluoroethylene (PTFE).

Clause 30: In some examples of the method of any one of clauses 24 to 29, the single bonding layer extends beyond the end of the hypotube and is bonded to the inner liner.

Clause 31: In some examples of the method of clause 30, the single bonding layer extends beyond the end of the hypotube substantially the same distance as the inner liner extends beyond the end of the hypotube.

Clause 32: In some examples of the method of any one of clauses 24 to 31, the metal or alloy includes at least one of stainless steel or a nickel-titanium alloy.

The details of one or more examples are set forth in the accompanying drawings and the description below. Other features, objects, and advantages will be apparent from the description and drawings, and from the claims.

DETAILED DESCRIPTION

The disclosure describes assemblies, systems, and techniques for attaching a hub to a catheter body to form a catheter. In some examples, the catheter may include a single bonding layer between the catheter body and the hub. The composition of the single bonding layer may be selected to bond tightly (e.g., create a fluid resistant interface) to the catheter body and the hub. For example, the single bonding layer may bond to a hypotube of the catheter body and the hub. In some examples, the single bonding layer also may bond to an inner liner attached to an inner circumferential surface of the hypotube.

By utilizing a single bonding layer selected to bond tightly to the catheter body and the hub, fewer interfaces between materials may be present in the catheter (e.g., compared to catheters that utilize multiple layers between the catheter body and the hub). Fewer interfaces may result in fewer potential failure points at which poor adhesion, delamination, or leaks may occur. Further, selecting a composition of the single bonding layer to form a tight bond between catheter body and the hub may reduce or substantially prevent (e.g., prevent or nearly prevent) poor adhesion, delamination, or leaks at the interfaces that are present. In this way, the single bonding layer between the catheter body and the hub may reduce or substantially prevent (e.g., prevent or nearly prevent) incidents of poor adhesion, delamination, or leaks at or near the hub of the catheter.

In some examples, the single bonding layer may include a polyamide or a polyether-co-polyamide. The hypotube may include a metal, such as titanium or stainless steel. The inner liner may include a polytetrafluoroethylene, and the hub may include polypropylene. The polyamide or polyether-co-polyamide may advantageously bond to a plurality of types of materials, including the titanium or stainless steel, the polypropylene, and, optionally, the polytetrafluoroethylene to join the hub to the hypotube and, optionally, the inner liner.

Figure 1:
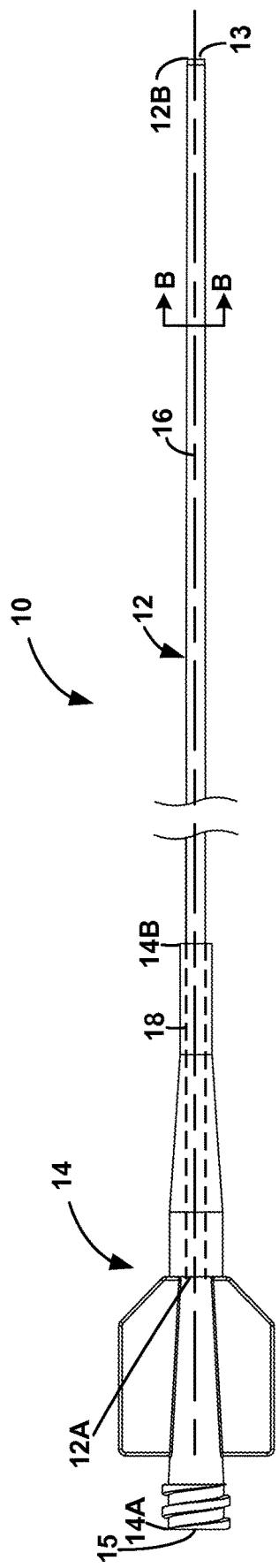
FIG. 1 is a side elevation view of an example catheter, which includes a catheter body including an inner liner and a hypotube, a hub, and a single bonding layer attaching the hub to the catheter body.

FIG. 1 is a side elevation view of an example catheter 10, which includes catheter body 12 and hub 14. Catheter hub 14 is positioned at a proximal end 12A of catheter body 12 and defines an opening 15 through which at least one inner lumen 26 (shown in FIG. 2) of catheter body 12 may be accessed and, in some examples, closed. For example, catheter hub 14 may include a luer connector for connecting to another device, a hemostasis valve, or another mechanism or combination of mechanisms. In some examples, catheter 10 includes a strain relief member, which may be a part of hub 14 or may be separate from hub 14. In other examples, catheter 10 may not include a strain relief member.

Catheter body 12 is an elongated body that extends from proximal end 12A to distal end 12B and defines at least one inner lumen 26 (e.g., one inner lumen, two inner lumens, three inner lumens, or more inner lumens) that terminates at distal opening 13 defined by catheter body 12. In the example shown in FIG. 1, proximal end 12A of catheter body 12 is received within hub 14 and is mechanically connected to hub 14 via a single bonding layer 18. Opening 15 defined by hub 14 and located at proximal end 14A of hub 14 is aligned with at least one inner lumen 26 of catheter body 12, such that the inner lumen of catheter body 12 may be accessed via opening 15.

Catheter body 12 has a suitable length for accessing a target tissue site within the patient from a vascular access point. The length may be measured along longitudinal axis 16 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 129 centimeters (cm) to about 135 cm, such as about 132 cm, although other lengths may be used.

In some examples, catheter body 12 may be used to access relatively distal locations in a patient, such as the middle cerebral artery (MCA) in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists and/or turns) through the vasculature to reach these tissue sites. Catheter body 12 may be structurally configured to be relatively flexible, pushable, and relatively kink- and buckle-resistant, so that catheter body 12 may resist buckling when a pushing force is applied to a relatively proximal portion of the catheter to advance the catheter body distally through vasculature, and so that catheter body 12 may resist kinking when traversing a tight turn in the vasculature Kinking and/or buckling of catheter body 12 may hinder efforts of a clinician to push the catheter body distally, e.g., past a turn.

In some examples, the diameter of at least one inner lumen 26 (shown in FIG. 2) of catheter body 12, also referred to herein as an inner diameter of catheter body 12, may be substantially constant from proximal end 12A to distal end 12B. In other examples, the inner diameter of catheter body 12 may taper from a first inner diameter at a proximal portion that includes proximal end 12A to a second inner diameter at a distal portion that includes distal end 12B, the second inner diameter being smaller than the first inner diameter.

In some examples, at least a portion of an outer surface of catheter body 12 includes at least one coating, including, but not limited to, an anti-thrombogenic coating, which may help reduce the formation of thrombi in vitro; an antimicrobial coating; or a lubricating coating. The lubricating coating may be configured to reduce static friction kinetic friction, or both between catheter body 12 and tissue of the patient as catheter body 12 is advanced through the vasculature. The lubricating coating can be, for example, a hydrophilic coating. In some examples, the entire working length of catheter body 12 (from distal portion 14B of hub 14 to distal end 12B) is coated with the hydrophilic coating. In other examples, only a portion of the working length of catheter body 12 coated with the hydrophilic coating. This may provide a length of catheter body 12 distal to distal end 14B of hub 14 with which the clinician may grip catheter body 12, e.g., to rotate catheter body 12 or push catheter body 12 through vasculature.

In accordance with some examples of this disclosure, hub 14 may be attached to catheter body 12 using single bonding layer 18. Single bonding layer 18 may extend substantially along an axial length (measured along longitudinal axis 16) of hub 14 between an inner circumferential surface of hub 14 and an outer circumferential surface of catheter body 12. In some examples, single bonding layer 18 may extend somewhat beyond distal end 14B of hub 14, and may be substantially aligned with an end of catheter body 12 within hub 14. In some examples in which single bonding layer 18 extends beyond distal end 14B of hub 14, single bonding layer 18 may act as a strain relief.

Single bonding layer 18 may include a composition selected to bond tightly to catheter body 12 and hub 14. As used herein, bond tightly refers to an interface that is bonded sufficiently intimately to resist fluid flow along the interface. For example, single bonding layer 18 may include a polyamide, a polyether-co-polyamide, polyurethane, or an acrylic butadiene styrene co-polymer. Example polyamides that may be utilized in single bonding layer 18 include those available under the trademark Grilamid®, Nylon 12-based materials available from ZEUS® Inc., Orangeburg, S.C. Example polyether-co-polyamides that may be utilized in single bonding layer 18 include those available under the trademark Pebax® from Arkema Technical Polymers, France. Example polyurethane elastomers that may be utilized in single bonding layer 18 include those available under the trademark Pellethane® 2363-75D from Lubrizol Thermedics Corp., Ohio.

By utilizing single bonding layer 18 selected to bond tightly to the catheter body and the hub, fewer interfaces between materials may be present in the catheter 10 (e.g., compared to catheters that utilize multiple layers between catheter body 12 and hub 14). Fewer interfaces may result in fewer potential failure points at which poor adhesion, delamination, or leaks may occur. Further, selecting a composition of single bonding layer 18 to form a tight bond between catheter body 12 and hub 14 may reduce or substantially prevent (e.g., prevent or nearly prevent) poor adhesion, delamination, or leaks at the interfaces that are present. In this way, single bonding layer 18 may reduce or substantially prevent (e.g., prevent or nearly prevent) incidents of poor adhesion, delamination, or leaks at or near hub 14 of catheter 10.

Figure 2:
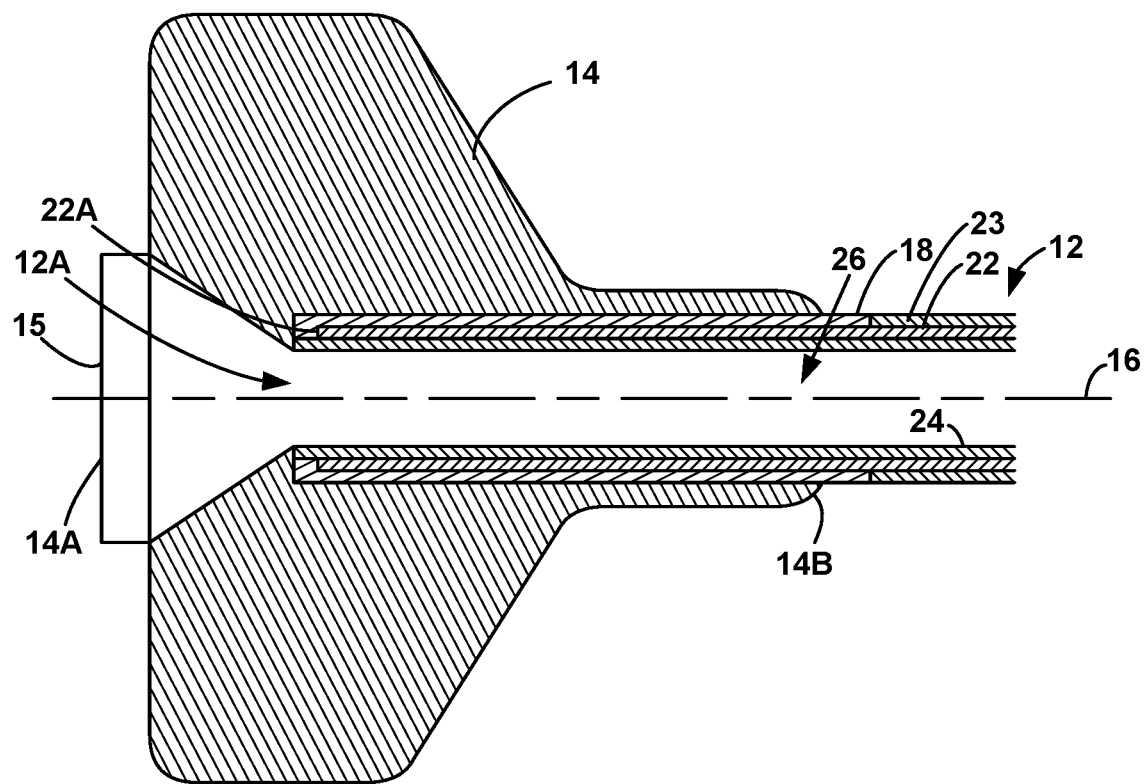
FIG. 2 is a cross-sectional diagram of a proximal portion of the catheter of FIG. 1.

FIG. 2 is a cross-sectional diagram of a proximal portion of catheter 10 of FIG. 1, which includes catheter body 12 including an inner liner 24 and a hypotube 22, hub 14, and single bonding layer 18 attaching hub 14 to catheter body 12. As shown in FIG. 2, catheter body 12 includes inner liner 24 and hypotube 22. Optionally, the catheter body may further include an outer jacket 23 that overlies the hypotube 22 along some or all of the length of the catheter body. For example, outer jacket 23 may extend from a proximal jacket end positioned distal of and/or adjacent to a distal end of the bonding layer 18, toward or to the distal end 12B of the catheter body 12. The catheter body 12 can include still other optional layers, instead of or in addition to the outer jacket 23. Hypotube 22 is configured to increase the structural integrity of catheter body 12 of a portion of catheter body 12 while allowing catheter body 12 to remain relatively flexible. For example, hypotube 22 may be configured to help catheter body 12 substantially maintain its cross-sectional shape or at least help prevent catheter body 12 from buckling or kinking as it is manipulated by a clinician. Hypotube 22, together with inner liner 24, may help distribute both pushing and rotational forces along a at least a portion of length of catheter body 12, which may help prevent kinking of catheter body 12 upon rotation of body 12 or help prevent buckling of catheter body 12 upon application of a pushing force to catheter body 12. As a result, a clinician may apply pushing forces, rotational forces, or both, to a proximal portion of catheter body 12, and such forces may cause a distal portion of catheter body 12 to advance distally, rotate, or both, respectively.

In the example shown in FIGS. 1 and 2, hypotube 22 may extend along only a portion of a length of catheter body 12. For example, a proximal end of hypotube 22 may be terminate proximal to distal end 14B of hub 14 and a distal end of hypotube 22 may terminate distal to distal end 14B of hub 14. As shown in FIG. 2, a proximal end 22A of hypotube 22 extends within hub 14 and terminates slightly distal of proximal end 12A of catheter body 12.

Hypotube 22 may include a metal, alloy or polymer. In some examples, the metal, alloy or polymer may be a biocompatible metal, alloy or polymer, clinically accepted for use in a body of a patient. For example, hypotube 22 may include at least one of stainless steel or a nickel-titanium alloy.

In some examples, hypotube 22 may define a substantially continuous (e.g., continuous or nearly continuous) cylinder, as shown in FIG. 2. In other examples, hypotube 22 may include a spiral-cut tube or a slotted tube, such that hypotube 22 includes gaps and is not substantially continuous. The spiral-cut or slotted tube may be effective to transfer at least one of axial, rotational, or bending forces along a length of catheter body 12, but may possess greater flexibility than a substantially continuous cylinder.

Catheter body 12 can also include an inner liner 24. Inner liner 24 can define at least one inner lumen 26 of catheter body 12, the at least one inner lumen 26 extending from proximal end 12A to distal end 12B and defining a passageway extending from proximal end 12A to distal opening 13 at distal end 12B of catheter body 12. At least one inner lumen 26 may be sized to receive a medical device (e.g., another catheter, a guidewire, a thrombectomy device, an embolic protection device, a stent, a delivery system for a stent or implant, or any combination thereof), a therapeutic agent, or the like. At least the inner surface of inner liner 24 defining at least one inner lumen 26 may be lubricious in some examples in order to facilitate the introduction and passage of a device, a therapeutic agent, or the like, through at least one inner lumen 26. For example, the material from which the entire inner liner 24 is formed may be lubricious, or inner liner 24 may be formed from two or more materials, where the material that defines at least one inner lumen 26 may be more lubricious than the material that interfaces with hypotube 22. In addition to, or instead of, being formed from a lubricious material, in some examples, an inner surface of inner liner 24 is coated with a lubricious coating.

Example materials from which inner liner 24 may be formed include, but are not limited to, a fluoropolymer, such as polytetrafluoroethylene (PTFE), perfluoroalkoxy alkane (PFA), fluorinated ethylene propylene (FEP), or any combination thereof. For example, inner liner 24 may be formed from an etched PTFE, e.g., may consist essentially of an etched PTFE.

In some examples, inner liner 24 defines a substantially constant (e.g., unvarying or nearly unvarying) inner diameter along the entire length of inner liner 24, while in other examples, inner liner 24 may define varying inner diameters.

A seamless inner liner 24 may be easier to slide over another device, e.g., another catheter or a guidewire, compared to a catheter formed from two or more longitudinal sections that are chemically or mechanically connected to each other because the seamless inner liner may define a smoother inner lumen 24. In contrast, joints between sections of an inner liner that are formed from two or more longitudinal sections may define surface protrusions or other irregularities along at least one inner lumen 26 which may interfere with the passage of devices through at least one inner lumen 26. In addition, a seamless inner liner 24 may help distribute pushing and rotational forces along the length of catheter body 12. Thus, the seamless inner liner 24 may help contribute to the pushability of catheter body 12.

As shown in FIG. 2, in some examples, inner liner 24 may extend proximal to proximal end 22A of hypotube 22. This portion of inner liner 24 thus may define an outer circumferential surface that is exposed and available to bond to single bonding layer 18.

Catheter 10 also includes hub 14. As shown in FIG. 2, hub 14 is attached to catheter body 12 by single bonding layer 18. Hub 14 may be formed of, in some examples, a polyolefin, such as polypropylene.

As shown in FIG. 2, hub 14 defines opening 15, and may include a taper from the proximal end 14A of hub 14, at which a connector may be defined (such as a threaded or slip-type luer connector) to the portion of hub 14 that contacts proximal end 12A of catheter body 12. In this way, opening 15 may include a taper and may substantially align with (e.g., align or nearly align with) with an inner surface of inner liner 24, which defines at least one inner lumen 26. Substantially aligning hub 14 and the inner surface of at least one inner liner 24 at proximal end 12A of catheter body 12 may reduce the chance that a medical instrument introduced into at least one inner lumen 26 via opening 15 may catch on proximal end 12A of catheter body 12.

In the example shown in FIG. 2, hub 14 is attached to catheter body 12 using single bonding layer 18. For example, single bonding layer 18 may attach hub 14 to the outer circumferential surface of hypotube 22, e.g., by a thermal bond or other type of bond. Single bonding layer 18 may extend along an axial length of hub 14 between an inner circumferential surface of hub 14 and an outer circumferential surface of catheter body 12. In some examples, single bonding layer 18 may be the only layer between the outer circumferential surface of hypotube 22 and the inner circumferential surface of hub 14.

In some examples, single bonding layer 18 may extend beyond distal end 14B of hub 14, as shown in FIG. 2. In some examples, a proximal end of single bonding layer 18 may be substantially aligned with a proximal end 12A of catheter body 12 within hub 14. For example, the proximal end of single bonding layer 18 may be substantially aligned with the proximal end of inner liner 24. In other words, single bonding layer 18 may extend beyond proximal end 22A of hypotube 22 substantially the same distance as inner liner 24 extends beyond the proximal end 22A of hypotube 22. In this way, in some examples, single bonding layer 18 may be attached to inner liner 24 near proximal end 12A of catheter body 12, e.g., by a thermal bond or other type of bond. By being attached or bonded to the proximal end of inner liner 24, single bonding layer 18 may mechanically stabilize the proximal end of inner liner 24. In some examples, single bonding layer 18 and inner liner 24 may substantially encapsulate hypotube 22 at proximal end 12A of catheter body 12. In some examples, this may reduce a chance of inner liner 24 detaching from hypotube 22 (for example, when a medical device is loaded into inner lumen 26 via opening 15 for delivery into the patient through catheter body 12), as the bond between single bonding layer 18 and inner liner 24 may help hold inner liner 24 against hypotube 22.

Single bonding layer 18 may include a composition selected to adhere tightly to hypotube 22, hub 14, and, in some examples, inner liner 24. For example, single bonding layer 18 may include a polyamide or a polyether-co-polyamide. As another example, single bonding layer 18 may consist essentially of polyamide or a polyether-co-polyamide, or may consist essentially of a polyether-co-polyamide.

In some examples, by utilizing a single bonding layer 18 rather than multiple layers including different materials selected to form bonds with hypotube 22 and hub 14, a total thickness of the structure between hypotube 22 and hub 14 may be decreased. For example, by utilizing single bonding layer 18, the spacing between hypotube 22 and hub 14 (the thickness of single bonding layer 18) may be on the order of thousandths of an inch, such as less than about 10 thousandths of an inch (about 0.010 inch; about 254 micrometers), such as about 5 thousandths of an inch (about 0.005 inch; about 127 micrometers).

Further, in some examples, hub 14 may be molded around catheter body 12. A single bonding layer 18 that includes a polyamide or polyether-co-polyamide may withstand the temperatures used to mold hub 14 (e.g., a polypropylene hub) without substantial amounts of degradation. This may further support the formation of a relatively tight (e.g., fluid resistant) bond between hypotube 22 and hub 14. In other examples, hub 14 may be adhesively bonded to catheter body 12 using single bonding layer 18.

By utilizing single bonding layer 18 selected to bond tightly to hypotube 22 the hub 14, fewer interfaces between materials may be present in the catheter 10 (e.g., compared to catheters that utilize multiple layers between hypotube 22 and hub 14). Fewer interfaces may result in fewer potential failure points at which poor adhesion, delamination, or leaks may occur. Further, selecting a composition of single bonding layer 18 to form a tight bond between hypotube 22 and hub 14 may reduce or substantially prevent (e.g., prevent or nearly prevent) poor adhesion, delamination, or leaks at the interfaces that are present. In this way, single bonding layer 18 may reduce or substantially prevent (e.g., prevent or nearly prevent) incidents of poor adhesion, delamination, or leaks at or near hub 14 of catheter 10. Further, utilizing a single bonding layer 18 between hypotube 22 and hub 14 may reduce a number of processing steps used to manufacture catheter 10, which may reduce a manufacturing cost for catheter 10.

Figure 3:
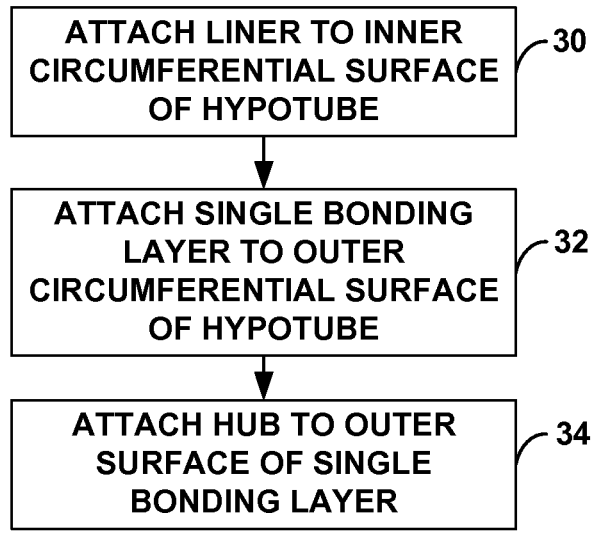
FIG. 3 is a flow diagram illustrating an example technique for forming a catheter that includes a catheter body including an inner liner and a hypotube, a hub, and a single bonding layer attaching the hub to the catheter body.

FIG. 3 is a flow diagram illustrating an example technique for forming a catheter that includes a catheter body including an inner liner and a hypotube, a hub, and a single bonding layer attaching the hub to the catheter body. The technique of FIG. 3 will be described with reference to catheter 10 of FIGS. 1 and 2. However, it will be understood that catheter 10 may be formed using other techniques, that the technique of FIG. 3 may be used to form other catheters, or both.

The technique of FIG. 3 includes attaching inner liner 24 to an inner circumferential surface of hypotube 22 (30). In some examples, inner liner 24 may be formed separately from hypotube 22, and the outer circumferential surface of inner liner 24 may be etched to facilitate attaching of inner liner 24 to hypotube 22. For example, the outer circumferential surface of inner liner 24 may be etched using a mixture of sodium and ammonia to prepare outer circumferential surface of inner liner 24 for attaching to inner circumferential surface of hypotube 22. In other examples, inner liner 24 may be attached to the inner circumferential surface of hypotube 22 using other techniques, such as coating techniques or the like.

The technique of FIG. 3 also may include attaching single bonding layer 18 to an outer circumferential surface of hypotube 22 (32). In some examples, single bonding layer 18 may be formed separate from hypotube 22 and laminated to the outer circumferential surface of hypotube 22. For example, single bonding layer 18 may be attached to the outer circumferential surface of hypotube 22 by forming a sheet of material, wrapping hypotube 22 with the sheet of material, heating the sheet of material, and pressing the sheet of material against the outer circumferential surface of hypotube 22 to attach the sheet of material to hypotube 22 and form single bonding layer 18. In other examples, single bonding layer 18 may be attached to the outer circumferential surface of hypotube 22 using other techniques, such as coating techniques or the like.

The technique of FIG. 3 further may include attaching hub 14 to an outer surface of single bonding layer 18 (34). In some examples, hub 14 may be molded over single bonding layer 18. For example, catheter body 12, including hypotube 22, single bonding layer 18, and, in some examples, inner liner 24, may be placed in a mold that defines the shape of hub 14, and hub 14 may be molded to catheter body 12. In other examples, hub 14 may be formed separately at attached to single bonding layer 18 using adhesive bonding, for example, by heating one or both of hub 14 or single bonding layer 18 to make the one or both of hub 14 or single bonding layer 18 tacky, using a solvent to make the one or both of hub 14 or single bonding layer 18 tacky, or the like.

Figure 4:
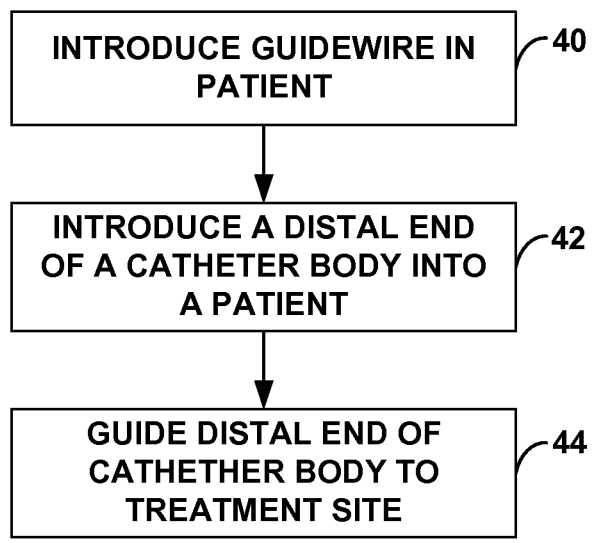
FIG. 4 is a flow diagram illustrating an example technique for utilizing a catheter that includes a catheter body including an inner liner and a hypotube, a hub, and a single bonding layer attaching the hub to the catheter body.

FIG. 4 is a flow diagram illustrating an example technique for utilizing a catheter that includes a catheter body including an inner liner and a hypotube, a hub, and a single bonding layer attaching the hub to the catheter body. The technique of FIG. 4 will be described with reference to catheter 10 of FIGS. 1 and 2. However, it will be understood that catheter 10 may be utilized using other techniques, that the technique of FIG. 4 may be used to utilize other catheters, or both.

The technique of FIG. 4 optionally includes introducing a guidewire in a body of a patient (40). The guidewire may define a pathway for catheter body 12 through the vasculature of the patient, and may aid in the navigation (e.g., steering and manipulation) of catheter 10 through the vasculature. In some examples, the guidewire may be introduced into vasculature (e.g., an intracranial blood vessel) of a patient via an access point (e.g., a femoral artery). For example, an inner lumen 26 of catheter body 12 may be configured to receive a guidewire, such that catheter body 12 may be guided through vasculature over the guidewire.

In some cases, in addition to optionally introducing a guidewire in the body of the patient (40), the technique of FIG. 4 may include advancing an inner catheter over the guidewire. The inner catheter may have a smaller outer diameter than catheter body 12. The inner catheter may, for example, help fill the space between the guidewire and the inner surface of catheter body 12 in order to help minimize the ledge effect, which may occur when a distal tip of catheter body 12, particularly the portion of the edge of the tip that tracks the outside of a curve formed by the body 12, engages with or abrades a wall of vasculature as catheter body 12 is advanced over the guidewire through a curve in the vasculature. The ledge effect may, at least in part, be attributable to unopposed space between the guidewire and inner lumen 26 of catheter body 12.

The technique of FIG. 4 also may include introducing a distal end 12B of catheter body 12 into the body of the patient (42) and guiding distal end 12B of catheter body 12 to a target tissue site within the patient (44). In some examples, distal end 12B of catheter may be introduced around a guidewire or an inner catheter, which may guide the distal end 12B of catheter 10 as catheter body 12 is advanced into the patient.

Once distal end 12B of catheter body 12 is positioned at the target tissue site, which may be proximal to thromboembolic material (e.g., a thrombus), the thromboembolic material be removed from the vasculature via catheter body 12. For example, the thromboembolic material may be aspirated from the vasculature by at least applying a vacuum force to inner lumen 24 of catheter body 12 via hub 14 (and/or proximal end 12A), which may cause the thromboembolic material to be introduced into inner lumen 24 via distal opening 13. Optionally, the vacuum or aspiration can be continued to thereby draw the thromboembolic material proximally along the inner lumen 24, all or part of the way to the proximal end 12A or hub 14. As a further option, the aspiration or vacuum may cause the thromboembolic material to attach or adhere to the distal tip; in such a case the catheter 10 or catheter body 12 and the thromboembolic material can be withdrawn from the vasculature together as a unit, for example through another catheter that surrounds the catheter 10 or catheter body 12.

As another example, the thromboembolic material may be removed from the vasculature using another technique, such as via an endovascular retrieval device delivered through the inner lumen 26 of the catheter body 12. In such a method the catheter body 12 can be inserted into the vasculature (for example using any technique disclosed herein) and the retrieval device advanced through the inner lumen 26 (or through another catheter, such as a microcatheter, inserted into the vasculature through the inner lumen 26) so that the device engages the thromboembolic material. The retrieval device and the material engaged thereby (together with any other catheter or microcatheter) can then be retracted into the inner lumen 26 and removed from the patient. Optionally, aspiration can be performed with or through the catheter body 12 during retraction of the retrieval device and thromboembolic material into the catheter body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

In other examples, instead of, or in addition to, using catheter 10 to remove thromboembolic material from vasculature, catheter 10 may be used to deliver a medical device (e.g., another catheter, a guidewire, a thrombectomy device, an embolic protection device, a stent, a delivery system for a stent or implant, or any combination thereof) to a treatment site through inner lumen 26, deliver a therapeutic agent (such as a liquid embolic material, or a drug such as a blood-thinning or thrombolytic agent) to the treatment site through inner lumen 26, or the like.

In some examples, catheter 10 or catheter body 12 may be a part of an assembly that includes, e.g., a guidewire and/or another catheter. The catheter 10 or catheter body 12 in such an assembly can be any of the embodiments or examples of the catheter 10 or catheter body 12 disclosed herein. The guidewire may be used to guide catheter 10 to a target tissue site within the vasculature of a patient. In addition, in some examples, the additional catheter of the assembly may also be configured to guide catheter 10 or body 12 to a target tissue site within the vasculature of a patient. The additional catheter of the assembly may be substantially similar (e.g. identical or nearly identical) in construction to catheter 10 (including any of the embodiments or examples of the catheter 10 disclosed herein), but may have proportionally greater or smaller dimensions, such that the catheter bodies of the catheters may nest together. For example, the additional catheter of the assembly may have a smaller outer diameter than catheter body 12 and may be placed and/or guided over the guidewire, and then catheter 10 or catheter body 12 may be guided over the additional catheter. The assembly may therefore include catheter 10 with an additional catheter positioned in the inner lumen 26 of catheter 10, and may further include a guidewire positioned in the inner lumen of the additional catheter.

Various examples have been described. These and other examples are within the scope of the following claims.

What is claimed is:

1. A catheter comprising:
   a hypotube defining an inner circumferential surface, an outer circumferential surface, and a proximal end, wherein the hypotube comprises a metal or an alloy;
   an inner liner attached to the inner circumferential surface of the hypotube and proximally extending beyond the proximal end of the hypotube, wherein the inner liner comprises a fluoropolymer;
   an outer jacket;
   a hub; and
   a single bonding layer adhesively bonding the outer circumferential surface of the hypotube to the hub, wherein the single bonding layer proximally extends beyond the proximal end of the hypotube substantially the same distance as the inner liner proximally extends beyond the proximal end of the hypotube such that a proximal end of the inner liner and a proximal end of the single bonding layer are aligned and the hub directly contacts the proximal end of the inner liner, wherein the single bonding layer comprises a polyamide or a polyether-co-polyamide, wherein the single bonding layer is the only layer between the outer circumferential surface of the hypotube and the hub and is the only layer between the inner liner and the hub proximal of the proximal end of the hypotube, and wherein the single bonding layer extends distally past the hub to a proximal end of the outer jacket.

2. The catheter of claim 1, wherein the single bonding layer consists essentially of the polyamide or the polyether-co-polyamide.

3. The catheter of claim 1, wherein the single bonding layer consists essentially of polyether-co-polyamide.

4. The catheter of claim 1, wherein the hub comprises polypropylene.

5. The catheter of claim 1, wherein the inner liner comprises polytetrafluoroethylene (PTFE).

6. The catheter of claim 1, wherein the single bonding layer is directly bonded to the inner liner proximal of the proximal end of the hypotube.

7. The catheter of claim 1, wherein the metal or the alloy comprises at least one of stainless steel or a nickel-titanium alloy.

8. The catheter of claim 1, wherein the hypotube comprises a spiral-cut tube or a slotted tube.

9. A catheter comprising:
   a hypotube defining an inner circumferential surface, an outer circumferential surface, and a proximal end, wherein the hypotube comprises a stainless steel or a nickel titanium alloy;
   an inner liner attached to the inner circumferential surface of the hypotube and proximally extending beyond the proximal end of the hypotube, wherein the inner liner comprises a polytetrafluoroethylene;
   an outer jacket;
   a hub; and
   a single bonding layer adhesively bonding the outer circumferential surface of the hypotube to the hub, wherein the single bonding layer consists essentially of a polyamide or a polyether-co-polyamide, wherein the single bonding layer proximally extends beyond the proximal end of the hypotube substantially the same distance as the inner liner proximally extends beyond the proximal end of the hypotube such that a proximal end of the inner liner and a proximal end of the single bonding layer are aligned and the hub directly contacts the proximal end of the inner liner, wherein the single bonding layer is adhesively bonded to the inner liner proximal to the proximal end of the hypotube, wherein the single bonding layer is the only layer between the outer circumferential surface of the hypotube and the hub and is the only layer between the inner liner and the hub proximal of the proximal end of the hypotube, and wherein the single bonding layer extends distally past the hub to a proximal end of the outer jacket.

10. The catheter of claim 9, wherein the hub comprises polypropylene.

11. The catheter of claim 9, wherein the hypotube comprises a spiral-cut tube or a slotted tube.

12. A method comprising:

attaching an inner liner to an inner circumferential surface of a hypotube, wherein the inner liner proximally extends beyond a proximal end of the hypotube, wherein the inner liner comprises a fluoropolymer, wherein the inner liner further defines an outer circumferential surface and a proximal end, and wherein the hypotube comprises a metal or an alloy;

attaching a single bonding layer to the outer circumferential surface of the hypotube, wherein the single bonding layer comprises a polyamide or a polyether-co-polyamide; and attaching a hub to an outer surface of the single bonding layer such that the single bonding layer adhesively bonds the outer circumferential surface of the hypotube to the hub, wherein the single bonding layer is the only layer between the hypotube and the hub and is the only layer between the inner liner and the hub proximal of the proximal end of the hypotube, wherein the single bonding layer proximally extends beyond the proximal end of the hypotube substantially the same distance as the inner liner proximally extends beyond the proximal end of the hypotube such that the proximal end of the inner liner and a proximal end of the single bonding layer are aligned and the hub directly contacts the proximal end of the inner liner, and wherein the single bonding layer extends distally past the hub to a proximal end of an outer jacket.

13. The method of claim 12, wherein the single bonding layer consists essentially of the polyamide or the polyether-co-polyamide.

14. The method of claim 12, wherein the single bonding layer consists essentially of polyether-co-polyamide.

15. The method of claim 12, wherein the hub comprises polypropylene.

16. The method of claim 12, wherein the inner liner comprises polytetrafluoroethylene (PTFE).

17. The method of claim 12, wherein the single bonding layer is directly bonded to the inner liner proximal of the proximal end of the hypotube.

* * * * *